US006383783B1

(12) United States Patent
Haddad

(10) Patent No.: US 6,383,783 B1
(45) Date of Patent: May 7, 2002

(54) NUCLEIC ACID ISOLATION BY ADHERING TO HYDROPHOBIC SOLID PHASE AND REMOVING WITH NONIONIC SURFACTANT

(75) Inventor: Louis C. Haddad, Mendota Heights, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/400,037

(22) Filed: Sep. 21, 1999

(51) Int. Cl.$^7$ .......................... C12P 19/34; C12Q 1/68; C12N 11/08; C07H 21/00

(52) U.S. Cl. ..................... 435/91.1; 435/6; 435/91.3; 435/180; 536/22.1

(58) Field of Search .................... 435/6, 89, 91.1, 435/91.3, 180; 536/22.1

(56) References Cited

U.S. PATENT DOCUMENTS

| | | | |
|---|---|---|---|
| 4,153,661 A | 5/1979 | Ree et al. ................. 264/120 |
| 4,373,519 A | 2/1983 | Errede et al. .............. 128/156 |
| 4,460,642 A | 7/1984 | Errede et al. .............. 428/283 |
| 4,483,920 A | 11/1984 | Gillespie et al. .............. 435/6 |
| 4,539,256 A | 9/1985 | Shipman ................. 428/315.5 |
| 4,565,663 A | 1/1986 | Errede et al. .............. 264/120 |
| 4,726,989 A | 2/1988 | Mrozinski ............... 428/315.5 |
| 4,810,381 A | 3/1989 | Hagen et al. ............ 210/502.1 |
| 4,906,378 A | 3/1990 | Hagen et al. .............. 210/635 |
| 4,923,978 A | 5/1990 | McCormick ................. 536/27 |
| 4,957,943 A | 9/1990 | McAllister et al. ........... 521/64 |
| 4,971,736 A | 11/1990 | Hagen et al. ................. 264/22 |
| 5,030,697 A | 7/1991 | Hugl et al. .............. 525/326.9 |
| 5,071,610 A | 12/1991 | Hagen et al. .............. 264/120 |
| 5,147,539 A | 9/1992 | Hagen et al. ............ 210/198.3 |
| 5,187,083 A | 2/1993 | Mullis ........................ 435/91 |
| 5,207,915 A | 5/1993 | Hagen et al. .............. 210/635 |
| 5,234,809 A | 8/1993 | Boom et al. .................. 435/91 |
| 5,238,621 A | 8/1993 | Hagen et al. .............. 264/45.3 |
| 5,279,742 A | 1/1994 | Markell et al. .............. 210/638 |
| 5,405,951 A | 4/1995 | Woodard ................. 536/25.41 |
| 5,438,127 A | 8/1995 | Woodard et al. ........... 536/25.4 |
| 5,438,128 A | 8/1995 | Nieuwkerk et al. ........ 536/25.4 |
| 5,438,129 A | 8/1995 | Woodard et al. ........... 536/25.4 |
| 5,472,600 A | 12/1995 | Ellefson et al. .............. 210/317 |
| 5,510,084 A | 4/1996 | Cros et al. .................. 422/104 |
| 5,525,319 A | 6/1996 | Woodard et al. ............ 423/277 |
| 5,543,305 A | 8/1996 | Cummins et al. .......... 435/91.1 |
| 5,585,236 A | 12/1996 | Bonn et al. ..................... 435/5 |
| 5,610,287 A | 3/1997 | Nikiforov et al. .......... 536/24.3 |
| 5,625,053 A | 4/1997 | Kresheck et al. ........ 536/25.41 |
| 5,637,687 A | 6/1997 | Wiggins ................... 536/25.4 |
| 5,786,208 A | 7/1998 | Clark et al. ................. 430/270 |
| 5,804,684 A | 9/1998 | Su ............................ 536/25.4 |
| 5,919,626 A | 7/1999 | Shi et al. ....................... 435/6 |
| 6,093,559 A | * 7/2000 | Bookbinder et al. ......... 435/183 |

FOREIGN PATENT DOCUMENTS

| | | |
|---|---|---|
| EP | 0 389 063 A1 | 9/1990 |
| EP | 0 389 063 B1 | 9/1990 |
| EP | 0 524 864 A1 | 1/1993 |
| EP | 0 524 864 B1 | 1/1993 |
| EP | 0 572 907 | 12/1993 |
| EP | 0 897 978 | 2/1999 |
| JP | 2-268 682 | 11/1990 |
| JP | 2-295 485 | 12/1990 |
| JP | 9-302 034 | 11/1997 |
| WO | WO 90/10637 | 9/1990 |
| WO | WO 92/18514 | 10/1992 |
| WO | WO 94/00464 | 1/1994 |
| WO | WO 97/07239 | 2/1997 |
| WO | WO 99/22021 | 5/1999 |
| WO | WO 99/23487 | 5/1999 |
| WO | WO 99/28504 | 6/1999 |

OTHER PUBLICATIONS

Altschuler et al., "Benchmarks: Plasmid DNA Isolation Utilizing a Novel Nonionic Detergent," *BioTechniques*, 17(3):434–435 (1994).

Bischoff et al., "Isolation of Specific tRNAs Using an Ionic–Hydrophobic Mixed–Mode Chromatographic Matrix," *Analytical Biochemistry*, 151:526–533 (1985).

Huber et al., "High–performance liquid chromatographic separation of detritylated oligonucleotides on highly cross–linked poly–(styrene–divinylbenzene) particles," *Journal of Chromatography*, 599:113–118 (1992).

Kroschwitz et al., eds., *Kirk–Othmer Encyclopedia of Chemical Technology*, 4$^{th}$ Ed., John Wiley & Sons, NY, 23:506–523 (1997).

Nielsen et al., "Peptide nucleic acid (PNA), a DNA mimic with a pseudopeptide backbone," *Chem. Soc. Rev.*, 26:73–78 (1997).

* cited by examiner

*Primary Examiner*—David M Naff
(74) *Attorney, Agent, or Firm*—MarySusan Howard; Robert W. Sprague

(57) ABSTRACT

Nucleic acids are isolated by adhering a target nucleic acid in a sample to a hydrophobic polymeric solid phase, and applying a nonionic surfactant to the solid phase to remove the target nucleic acid from the solid phase. The solid phase may be made of polyethylene, polypropylene, or polytetrafluoroethylene, and be in the form of a porous matrix. Nonionic surfactants include polyoxyethylene surfactants and polyoxyethylene-co-oxypropylene surfactants. A buffer containing a salt that enhances binding of the nucleic acid to the solid phase may be added to the solid phase with or prior to the sample containing the nucleic acid. When the sample contains cells, the cells are lysed to release contents of the cells as a lysate containing nucleic acids. A kit is formed containing the solid phase and nonionic surfactant, and may also include a flow-through receptacle. Nucleic acids in a sample can be prevented from adhering to a hydrophobic polymeric surface by applying a nonionic surfactant to the surface before the sample is contacted with the surface.

32 Claims, No Drawings

NUCLEIC ACID ISOLATION BY ADHERING TO HYDROPHOBIC SOLID PHASE AND REMOVING WITH NONIONIC SURFACTANT

BACKGROUND

The isolation and purification of nucleic acids (DNA and RNA, for example) from complex matrices such as blood, bacterial cell culture media, and forensic samples is an important process in genetic research, nucleic acid probe diagnostics, forensic DNA testing and other areas. The separation of single-stranded from double-stranded DNA, and of bound from unbound nucleic acid hybridization probes are also important techniques in these areas. A variety of methods for preparing nucleic acids are known in the art; however, each has its limitations.

Traditionally a phenol chloroform extraction has been used, but this requires the use of toxic and corrosive chemicals and is not easily automated. Solid phase extraction has also been used for nucleic acid purification. For example, Boom et al. (U.S. Pat. No. 5,234,809) describe a method for isolating nucleic acids from a nucleic acid source in which a suspension of silica particles is mixed with a buffered chaotropic agent such as guanidinium thiocyanate in a reaction vessel followed by addition of the sample and thorough mixing. In the presence of the chaotrope, the nucleic acids are adsorbed onto the silica, which is separated from the liquid phase by centrifugation, washed with an alcohol water mix, and finally eluted using a dilute aqueous buffer. Silica solid phase extraction requires the use of the alcohol wash step to remove residual chaotrope without eluting the nucleic acid; however, great care must be taken to remove all traces of the alcohol (by heat evaporation or washing with another very volatile and flammable solvent) in order to prevent inhibition of sensitive enzymes used to amplify or modify the nucleic acid in subsequent steps.

Ion exchange methods, such as those offered by Qiagen (Valencia, Calif. 91355), produce high quality nucleic acids. However, these result in the presence of high levels of salts which must be removed before the nucleic acids can be further utilized.

SUMMARY

The present invention provides methods for the isolation, including concentration, and preferably purification and recovery of nucleic acids. It also provides methods for the reduction in the amount of nucleic acid that adheres to a surface. In one embodiment, the method involves adhering nucleic acid to a hydrophobic organic polymeric material, such as polypropylene powder and polytetrafluoroethylene fibrils, and removing (e.g., eluting) the nucleic acids from such hydrophobic materials with a nonionic surfactant. In another embodiment, a nonionic surfactant is used to treat a hydrophobic surface to reduce, and preferably prevent, the adhesion of nucleic acids to hydrophobic surfaces.

Nucleic acids isolated according to the invention, will be useful, for example, in assays for detection of the presence of a particular nucleic acid in a sample. Such assays are important in the prediction and diagnosis of disease, forensic medicine, epidemiology, and public health. For example, isolated DNA may be subjected to hybridization and/or amplification to detect the presence of an infectious virus or a mutant gene in an individual, allowing determination of the probability that the individual will suffer from a disease of infectious or genetic origin. The ability to detect an infectious virus or a mutation in one sample among the hundreds or thousands of samples being screened takes on substantial importance in the early diagnosis or epidemiology of an at-risk population for disease, e.g., the early detection of HIV infection, cancer or susceptibility to cancer, or in the screening of newborns for diseases, where early detection may be instrumental in diagnosis and treatment. In addition, the method can also be used in basic research laboratories to isolate nucleic acid from cultured cells or biochemical reactions. The nucleic acid can be used for enzymatic modification such as restriction enzyme digestion, sequencing, and amplification.

In one preferred embodiment, a method for isolating nucleic acid from a sample includes: introducing a sample comprising target nucleic acid (e.g., DNA, RNA, PNA) to a hydrophobic organic polymeric solid phase to adhere at least a portion of the target nucleic acid to the solid phase; and applying a nonionic surfactant to the solid phase to remove at least a portion of the adhered target nucleic acid. Preferably, the sample is a biological sample, which include, for example cells. In certain embodiments, prior to introducing the biological sample, the method includes lysing the cells to release the contents of the cells as a lysate that includes nucleic acid.

In certain embodiments, the method further includes introducing a binding buffer comprising an added salt to the hydrophobic organic polymeric solid phase to assist in adhering the nucleic acid to the solid phase. Preferably, the binding buffer is introduced prior to introducing the sample. In certain embodiments, the method further includes washing the solid phase having nucleic acid adhered thereto to remove non-nucleic acid components of the sample. Such washing is typically with a washing buffer, comprising an added salt.

The hydrophobic organic polymeric solid phase material preferably includes a fluorinated polymer such as polytetrafluoroethylene. More preferably it includes a polyolefin such as polyethylene or polypropylene. The nonionic surfactant is preferably a polyoxyethylene surfactant and more preferably a polyoxyethylene-co-oxypropylene surfactant.

The present invention also provides a method for isolating double-stranded DNA from a sample. The method includes: introducing a sample comprising double-stranded DNA to a hydrophobic organic polymeric solid phase to adhere at least a portion of the double stranded DNA to the solid phase; washing the solid phase having double-stranded DNA adhered thereto to remove non-double-stranded DNA components of the sample (including single-stranded DNA); and applying a nonionic surfactant to the solid phase to remove at least a portion of the adhered double-stranded DNA. Thus, the methods of the present invention include the separation of various types of nucleic acid.

The present invention also provides a method for reducing the amount of (and preferably preventing) nucleic acid that adheres to a hydrophobic organic polymeric surface. The method includes applying a nonionic surfactant to the hydrophobic organic polymeric surface, washing the surface with a solvent (such as water or other solvent, such as that in which the surfactant is dissolved), and contacting the surface with a sample comprising the nucleic acid.

The present invention also provides a kit that includes a hydrophobic organic polymeric solid phase to which nucleic acid will adhere and a nonionic surfactant capable of removing at least a portion of the nucleic acid from the solid phase. Preferably, the kit further includes a flow-through receptacle.

Definitions

"Nucleic acid" shall have the meaning known in the art and refers to both DNA and RNA, in a wide variety of forms, including, without limitation, double-stranded or single-stranded configurations, circular form, plasmids, relatively short oligonucleotides, peptide nulceic acids also called PNA's (as described in Nielsen et al., *Chem. Soc. Rev.*, 26, 73–78 (1997)), and the like.

"Isolated" refers to nucleic acid that has been removed from the sample in which it is originally found. This includes simply concentrating the desired nucleic acid without necessarily removing any other materials other than the original solvent in the original sample. It also includes separating desired nucleic acid from other materials, e.g., cellular components such as proteins, lipids, salts, etc. More preferably, the isolated nucleic acid is substantially purified. "Substantially purified" refers to nucleic acid that is at least 50%, preferably at least 80%, and more preferably at least 95%, pure with respect to removal of a contaminant, e.g., cellular components such as protein, lipid, or salt. These percentages refer to the amount of target nucleic acid (e.g., DNA, RNA, PNA) relative to the total amount of the target nucleic acid plus other (non-target) nucleic acid and contaminants, e.g., cellular components such as proteins, lipids, salts, etc., other than the solvent in the sample. Thus, the term "substantially purified" generally refers to separation of a majority of cellular components or reaction contaminants from the sample, so that compounds capable of interfering with the subsequent use of the isolated nucleic acid are removed.

"Adheres to" or "adherance" or "binding" refers to reversible binding via a wide variety of mechanisms, including weak forces such as Van der Waals interactions, electrostatic interactions, affinity binding, or physical trapping. The use of this term does not imply a mechanism of action, and includes adsorptive and absorptive mechanisms.

"Hydrophobic organic polymeric solid phase" refers to a polymer made of repeating units, which may be the same or different, of organic compounds of natural and/or synthetic origin. This includes homopolymers and heteropolymers (e.g., copolymers, terpolymers, tetrapolymers, etc., which may be random or block, for example). A hydrophobic polymer has a critical surface tension of less than the surface tension of water (e.g., less than about 72 dynes/cm), and preferably less than the critical surface tension of nylon (e.g., less than about 43 dynes/cm). This term includes fibrous or particulate forms of a polymer, which can be readily prepared by methods well-known in the art. Such materials typically form a porous matrix, although for certain embodiments, the solid phase also refers to a solid surface, such as a nonporous sheet of organic polymeric material.

"Surfactant" refers to a substance that lowers the surface or interfacial tension of the medium in which it is dissolved. "Nonionic surfactant" refers to a surfactant molecule whose polar group is not electrically charged.

DETAILED DESCRIPTION OF PREFERRED EMBODIMENTS

It has been found that nucleic acids will adhere to hydrophobic organic polymeric materials, such as polypropylene powder and polytetrafluoroethylene fibrils, and that nucleic acids can be effectively removed from such hydrophobic materials with a nonionic surfactant. Furthermore, a nonionic surfactant can be used to treat a hydrophobic organic polymeric surface, such as a plastic sheet, to reduce, and preferably prevent, the adhesion of nucleic acids to hydrophobic surfaces.

The methods of the present invention can be used to isolate nucleic acids from a wide variety of samples, particularly biological samples such as body fluids (e.g., whole blood, blood serum, urine, saliva), various tissues, cell cultures, etc. The type of sample is not a limitation of the present invention. Biological samples are those of biological or biochemical origin. Those suitable for use in the methods of the present invention can be derived from mammalian, plant, bacterial, or yeast sources. The biological sample can be in the form of single cells or in the form of a tissue. Cells or tissue can be derived from in vitro culture.

For samples containing cells, the cell membranes are initially lysed to release the contents of the cells as a lysate containing nucleic acid. Lysis herein is the physical disruption of the membranes of the cells, referring to the outer cell membrane and, when present, the nuclear membrane. This can be done using standard techniques, such as by boiling, by treatment with chaotropic agents, by physical disruption or freeze/thawing. Typically, to isolate nucleic acids from a cell lysate, it is preferable to remove the proteins first. This can be done, for example, by treating with azlactone beads (e.g., those of the type commercially available as EMPHAZE AB1 beads from 3M Company, St. Paul, Minn. or those of the type disclosed in International Publication No. WO 94/00464 (3M Company)) or passing the sample through a cation exchange membrane or column at a pH sufficiently low to maintain the positive charge of the proteins.

The nucleic acids may be isolated (e.g., concentrated or separated from contaminants) according to the invention from an impure, partially pure, or a pure sample. The purity of the original sample is not critical, as nucleic acid may be isolated from even grossly impure samples. For example, nucleic acid may be removed from an impure sample of a biological fluid such as blood, saliva, or tissue. If an origincal sample of higher purity is desired, the sample may be treated according to any conventional means known to those of skill in the art prior to undergoing isolation according to the invention. For example, the sample may be processed so as to remove certain impurities such as insoluble materials prior to nucleic acid isolation.

The nucleic acid isolated as described herein may be of any molecular weight and in single-stranded form, double-stranded form, circular, plasmid, etc. Various types of nucleic acid can be separated from each other (e.g., RNA from DNA, or double-stranded DNA from single-stranded DNA). For example, small oligonucleotides or nucleic acid molecules of about 10 to about 50 bases in length, much longer molecules of about 1000 bases to about 10,000 bases in length, and even high molecular weight nucleic acids of about 50 kb to about 500 kb can be isolated using the methods of the present invention. In some aspects, a nucleic acid isolated according to the invention may preferably be in the range of about 10 bases to about 100 kilobases.

The nucleic acid sample applied to the hydrophobic organic solid phase material according to the methods described herein may be in a wide variety of volumes. For example, the applied volume may be as large as 1 liter or as small as 1 $\mu$L. It could also be utilized in a microfluidic format (the so called "lab on a chip") in which very small volumes (less than 1 $\mu$L) are used. The nucleic acid applied to the solid phase matrix, as described herein, may be any amount, that amount being determined by the amount of solid phase. Preferably, the amount of nucleic acid applied to the solid phase is less than the dried weight of the solid phase, typically about $1/10,000$ to about $1/100$ (weight nucleic acid/solid phase). The amount of nucleic acid applied to the solid phase may be as much as 100 grams or as little as 1 picogram, for example.

The desired nucleic acid isolated from the solid phase material is preferably in an amount of about 30%, more preferably, about 70%, and most preferably, about 90%, or more than the amount of desired nucleic acid originally applied to the solid phase. Thus, the methods of the present invention provide for high recovery of the desired or target nucleic acid from a sample. Furthermore, exceedingly small amounts of nucleic acid molecules may be quantitatively recovered according to the invention. The recovery or yield is mainly dependent on the quality of the sample rather than the procedure itself. Because the invention provides a nucleic acid preparation that does not require concentration from a large volume, the invention avoids risk of loss of the nucleic acid.

Typically, a sample containing nucleic acid is added to the hydrophobic organic polymeric solid phase material in a flow-through receptacle, although this receptacle is not a necessary requirement. The nucleic acid then adheres to the hydrophobic organic polymeric solid phase material. Preferably, the binding of the nucleic acid may be enhanced by the use of a binding buffer, which can be added with or prior to the sample containing the target nucleic acid. Such a buffer typically includes a standard biological buffer that is compatible with nucleic acid and has a pH of about 3 to 11. Examples include AMPSO (3-[(1,1dimethyl-2-hydroxyethyl)amino]-2-hydroxypropanesulfonic acid (#A7585, Sigma Chemical Co, St. Louis, Mo. 63178), MES (2-[N-morpholino]ethansulfonic acid) (#M5287, Sigma Chemical Co, St. Louis, Mo. 63178), or PBS (phosphate buffered saline) (typically at about 20 Millimolar (mM) salt concentration). The binding buffer also typically includes added salt to promote hydrophobic binding. Examples include sodium salts of phosphate, perchlorate, citrate, or sulfate, at concentrations up to about 400 mM or even 1 molar, for example. Preferably, unbound materials, such as digested proteins, lipids, and other unwanted cellular components are then separated from the adhered nucleic acid by washing the nucleic acid/solid phase material with a buffer, for example. This washing buffer is typically a biological buffer that is compatible with the nucleic acid and typically within a pH range of about 3 to about 11. Examples of suitable washing buffers for removing undesirable materials include those listed above for the binding buffer. Such a buffer may or may not include added salts, such as those listed above for the binding buffer. Once these materials are removed, the nucleic acid may be recovered by removing (as by eluting) them from the solid phase material with a nonionic surfactant, which may be in an eluting buffer, e.g., such as those listed above (without added salt). Using this preferred method, the recovered nucleic acid is substantially pure, concentrated, and suitable for immediate use in subsequent experiments (e.g., sequencing experiments).

The hydrophobic organic polymeric solid phase material useful in the methods of the present invention may be a wide variety of organic materials that reversibly bind nucleic acid. Examples of suitable polymers include for example, polyolefins and fluorinated polymers. The solid phase material is typically washed to remove salts and other contaminants prior to use. It can either be stored dry or in aqueous suspension ready for use. The solid phase material is preferably used in a flow-through receptacle, for example, such as a pipet, syringe, or larger column, microtiter plate, or microfluidic device, although suspension methods that do not involve such receptacles could also be used.

The hydrophobic organic polymeric solid phase material useful in the methods of the present invention can include a wide variety of materials in a wide variety of forms. For example, it can be in the form of particles, which may be loose or immobilized, fibers, a microporous film, or membrane. For flow-through applications of the present invention, such materials are typically in the form of a porous matrix. Preferably, for such applications, the solid phase material has a relatively high surface area, such as, for example, more than one meter squared per gram ($m^2/g$). For applications that do not involve the use of a flow-through device, such as pretreatment of a solid surface to prevent adhesion of nucleic acid, the solid phase material may or may not be in porous matrix.

In one embodiment, the solid phase material includes a fibril matrix, which may or may not have particles enmeshed therein. If both a fibril matrix and particles are used, at least one of them is hydrophobic and capable of binding the desired (i.e., target) nucleic acid. The fibril matrix can include any of a wide variety of fibers. Typically, the fibers are insoluble in an aqueous environment. Examples include glass fibers, polyolefin fibers, particularly polypropylene and polyethylene microfibers, aramid fibers, a fluorinated polymer, particularly, polytetrafluoroethylene fibers, and natural cellulosic fibers. Mixtures of fibers can be used, which may be active or inactive toward binding of nucleic acid. Preferably, the fibril matrix forms a web that is at least about 15 microns, and no greater than about 1 millimeter, and more preferably, no greater than about 500 microns thick.

If used, the particles are typically insoluble in an aqueous environment. They can be made of one material or a combination of materials, such as in a coated particle. They can be swellable or nonswellable, although they are preferably nonswellable in water and organic liquids. Preferably, if the particle is doing the adhering, it is made of nonswelling, hydrophobic material. They can be chosen for their affinity for the target nucleic acid. Examples of some water swellable particles are described in U.S. Pat. No. 4,565,663 (Errede et al.), U.S. Pat. No. 4,460,642 (Errede et al.), and U.S. Pat. No. 4,373,519 (Errede et al.). Particles that are nonswellable in water are described in U.S. Pat. No. 4,810,381 (Hagen et al.), U.S. Pat. No. 4,906,378 (Hagen et al.), U.S. Pat. No. 4,971,736 (Hagen et al.); and U.S. Pat. No. 5,279,742 (Markell et al.). Preferred particles are polyolefin particles, such as polypropylene particles (e.g., powder). Mixtures of particles can be used, which may be active or inactive toward binding of nucleic acid.

If coated particles are used, the coating is preferably an aqueous- or organic-insoluble, nonswellable material. The coating may or may not be one to which nucleic acid will adhere. Thus, the base particle that is coated can be inorganic or organic. The base particles can include inorganic oxides such as silica, alumina, titania, zirconia, etc., to which are covalently bonded organic groups. For example, covalently bonded organic groups such as aliphatic groups of varying chain length (C2, C4, C8, or C18 groups) can be used.

Examples of suitable solid phase materials that include a fibril matrix are described in U.S. Pat. No. 5,279,742 (Markell et al.), U.S. Pat. No. 4,906,378 (Hagen et al.), U.S. Pat. No. 4,153,661 (Ree et al.), U.S. Pat. No. 5,071,610 (Hagen et al.), U.S. Pat. No. 5,147,539 (Hagen et al.), U.S. Pat. No. 5,207,915 (Hagen et al.), and U.S. Pat. No. 5,238,621 (Hagen et al.). Those that include a polytetrafluoroethylene matrix (PTFE) are particularly preferred.

The PTFE matrix can be prepared according to the procedure described in U.S. Pat. No. 4,906,378 (Hagen et al.). Briefly, this involves the steps of blending the particulate material with a polytetrafluoroethylene aqueous dispersion in the presence of sufficient lubricant water to exceed the absorptive capacity of the solids, yet maintain a putty-like consistency, subjecting the putty-like mass to intensive mixing at a temperature of about 50° C. to about 100° C. to cause initial fibrillation of the polytetrafluoroethylene particles, biaxially calendering the putty-like mass to cause additional fibrillation of the polytetrafluoroethylene particles while maintaining the same water content, and drying the resultant sheet.

In another preferred embodiment, the solid phase (e.g., a microporous thermoplastic polymeric support) has a microporous structure characterized by a multiplicity of spaced, randomly dispersed, nonuniform shaped, equiaxed particles of thermoplastic polymer connected by fibrils. Particles are spaced from one another to provide a network of micropores therebetween. Particles are connected to each other by fibrils, which radiate from each particle to the adjacent particles. Either, or both, the particles or fibrils may be hydrophobic and allow for adherance of nucleic acids. Examples of preferred such materials have a high surface area, often as high as 40 meters$^2$/gram as measured by Hg surface area techniques and pore sizes up to about 5 microns.

This type of fibrous material can be made by a preferred technique that involves involves the use of induced phase separation. This involves melt blending a thermoplastic polymer with an immiscible liquid at a temperature sufficient to form a homogeneous mixture, forming an article from the solution into the desired shape, cooling the shaped article so as to induce phase separation of the liquid and the polymer, and to ultimately solidify the polymer and remove a substantial portion of the liquid leaving a microporous polymer matrix. This method and the preferred materials are described in detail in U.S. Pat. No. 4,726,989 (Mrozinski), U.S. Pat. No. 4,957,943 (McAllister et al.), and U.S. Pat. No. 4,539,256 (Shipman). Such materials are referred to as thermally induced phase separation membranes (TIPS membranes) and are particularly preferred.

The affinity of the nucleic acids for the hydrophobic solid phase polymer can be controlled by the concentration of salt used during the binding or adhering of nucleic acids to the solid phase (which can be controlled through the use of a buffer referred to herein as a binding buffer), or the concentration of salt used during the elution step (which can be controlled through the use of a buffer referred to herein as an elution buffer). If desired, the binding and elution buffers, which typically are within a pH range of about 3 to about 11, can be used to separate different forms of nucleic acids. Depending on the solid phase, the binding of different types of nucleic acids can be controlled by the nature of the binding and elution buffers. High concentrations of salts, such as phosphates, will generally increase the binding capacity of solid supports such as polypropylene particulate. In some cases this can be used to separate different forms of nucleic acids.

A preferred aqueous solution for releasing the nucleic acids from the solid phase to form a solution containing nucleic acids includes a sufficient concentration of one or more nonionic surfactants. A preferred solution for releasing the nucleic acid includes water and a minimal amount of a buffer, such as PBS, to maintain the required pH and a minimal amount of nonionic surfactant. This minimal amount will depend upon which nonionic surfactant is used. For PLURONIC F68, this amount is no less than about 0.06 mM. In general, the concentration of nonionic surfactant needed for efficient elution must be higher than the critical micelle concentration (i.e., the minimum concentration of surfactant in water required to make a micelle, e.g., a submicroscopic aggregation of surfactant molecules) for that surfactant. Elution flow rate is not critical as long as there is enough time for the nucleic acid to desorb from the solid support.

A wide variety of suitable nonionic surfactants are known. They include, for example, polyoxyethylene surfactants, carboxylic ester surfactants, carboxylic amide surfactants, etc. Commercially available nonionic surfactants include, n-dodecanoylsucrose, n-dodecyl-β-D-glucopyranoside, n-octyl-β-D-maltopyranoside, n-octyl-β-D-thioglucopyranoside, n-decanoylsucrose, n-decyl-β-D-maltopyranoside, n-decyl-β-D-thiomaltoside, n-heptyl-β-D-glucopyranoside, n-heptyl-β-D-thioglucopyranoside, n-hexyl-β-D-glucopyranoside, n-nonyl-β-D-glucopyranoside, n-octanoylsucrose, n-octyl-β-D-glucopyranoside, cyclohexyl-n-hexyl-β-D-maltoside, cyclohexyl-n-methyl-β-D-maltoside, digitonin, and those available under the trade designations PLURONIC, TRITON, TWEEN, as well as numerous others commercially available and listed in the Kirk Othme Technical Encyclopedia. Preferred surfactants are the polyoxyethylene surfactants. More preferred surfactants are the polyoxyethylene co-oxypropylene surfactants.

According to a preferred embodiment of the present invention, a step is provided for recovering nucleic acids in a substantially purified form. This embodiment contemplates recovery methods that involve removal of either all of the eluate or aliquots of the eluate solution containing substantially purified nucleic acid released from the solid phase material. Such aliquots can be subjected to a variety of analytical and synthetic techniques known to one of skill in the art.

Examples of devices for using the methods of the present invention include standard laboratory filter holders and filters furnished by companies such as Millipore, Inc. (Bedford, Mass. 01730), Bio-Rad, Inc. (Hercules, Calif. 94547), Osmonics, Inc. (Westborough, Mass. 01581), and Whatman, Inc. (Clifton, N.J. 07014). The method of the invention can be conducted in filtration devices which facilitate the movement of solutions through filters (referred to as flow-through devices) by means including centrifugation, suction, pressure. Other devices include microtiter plates and microfluidic devices.

The present invention also provides a kit, which includes a solid support either with or without a holder (for example, a filter holder such as a syringe filter holder or a spin filter holder, or a column with retaining frits at each end for retaining particulate material), a nonionic surfactant, either neat or in a solution, and instructions for binding and eluting the nucleic acid. Preferably, the present invention provides kits that include a flow-through receptacle having a hydrophobic solid phase organic polymeric material therein and a nonionic surfactant.

The present invention also provides a method for reducing or preventing adhesion of nucleic acid to a hydrophobic organic material. However, unlike JP 2268682 (Hitachi Ltd.), which includes a nonionic surfactant in a mixture with the nucleic acid, the method of the present invention involves pretreating the material with a surfactant, preferably washing the material, and then contacting the material with the nucleic acid.

Objects and advantages of this invention are further illustrated by the following examples, but the particular materials and amounts thereof recited in these examples, as well as other conditions and details, should not be construed to unduly limit this invention.

EXAMPLES

Materials

DNA. Unless otherwise stated the DNA used in these experiments was calf thymus DNA (Sigma Chemical Co., St. Louis, Mo. 14508).

Plasmid DNA. PUC119 plasmid DNA was prepared by ATG Laboratories, Eden Prairie, Minn. 55344. This was dissolved to a concentration of about 30 µg/mL in either 10 or 400 mM phosphate buffer at pH 6.8.

Hydroxyapatite (HAP). HTP hydroxyapatite was obtained from Bio-Rad Co., Hercules, Calif. 94547.

Phosphate Buffer. All phosphate buffers used were prepared from equimolar amounts of mono and dibasic potassium phosphate.

Surfactant. PLURONIC F68 nonionic surfactant (BASF Corp. Parsippany, N.J. 07054).

Hydroxyapatite-loaded EMPORE membrane containing about 90% by weight HAP was made by the method of Example 1 in U.S. Pat. No. 4,906,378.

Polypropylene-loaded EMPORE membrane was made by the method of Example 1A in U.S. Pat. No. 5,071,610, except that polypropylene was used.

C18-loaded EMPORE membrane is commercially available from 3M Co. (St. Paul, Minn.).

Thermally induced phase separation membrane filters (TIPS membranes) are high surface area (up to 40 square meters per gram) polymer membranes with pore sizes in the micron to sub-micron range. The membranes used in these experiments were made of polypropylene (made according to Examples 1–4 of U.S. Pat. No. 4,726,989) or polyethylene (made according to Example 8C of U.S. Pat. No. 4,539,256).

Example 1

Comparison of DNA Adherance Characteristics for HAP in a Conventional Chromatography Column and Incorporated into an EMPORE Membrane HAP was incorporated into a conventional chromatography column as follows: 100 mg of HAP was placed in a standard 2 mL chromatography column (Bio-Rad Co., Hercules, Calif. 94547) mounted on a vacuum manifold. This was washed with 3 mL of 500 mM phosphate buffer followed by 5 mL of 50 mM phosphate buffer. Following this, 1 mL of 53 µg/mL DNA in 50 mM phosphate buffer was applied to the column which was then washed with 2 mL of 50 mM phosphate buffer followed by elution with 1 mL of 300 mM phosphate buffer. Filtrates from each step were monitored for absorbance at 260 nm (the absorption maximum for DNA).

Two 25 mm disks of the HAP-loaded EMPORE membrane (containing only HAP and PTFE fibrils) were placed in a syringe filter holder and washed with high and low phosphate buffer (3 mL of 500 mM phosphate buffer followed by 5 mL of 50 mM phosphate buffer). Following this, 2 mL of a 22 µg/ml DNA in 50 mM phosphate were applied to the disks which were then washed with 2 mL of 50 mM phosphate followed by 2 mL of 300 mM phosphate followed by 2 mL of 50 mM phosphate and 2 mL of 1.0 M phosphate buffer. Again the level of DNA in the filtrates was determined by monitoring the absorbance at 260 nm. The results, reported as the absorbance at 260 nm, were as follows:

| Sample | HAP in column | HAP in Empore |
| --- | --- | --- |
| Challenge DNA solution | 0.5 | 0.23 |
| Challenge filtrate | <0.03 | <0.03 |
| 50 mM phosphate wash | 0.03 | <0.03 |
| 300 mM phosphate wash | 0.5 | <0.03 |
| 50 mM phosphate wash | — | <0.03 |
| 1.0M phosphate wash | — | <0.03 |

At low phosphate concentration (50 mM) the DNA adhered to the HAP in the column and eluted when the phosphate concentration was raised to 300 mM. However, the results with the HAP loaded EMPORE membrane were unexpected. Although the DNA adhered under low phosphate conditions it would not elute at the higher phosphate concentrations. Subsequent experiments showed that DNA would adhere to this membrane even when dissolved in 400 mM phosphate. Furthermore, X-ray diffraction studies showed that the HAP was not altered when it was incorporated into the membrane. The DNA was bound to the polytetrafluoroethylene fibrils of the EMPORE membrane and not the HAP particles at such high phosphate concentrations.

Example 2

DNA Adherance and Elution on a HAP-Loaded EMPORE Membrane

A single 25 mm disk of a HAP-loaded EMPORE membrane in a syringe filter holder was charged with 2 mL of about 35 µg/mL DNA in 50 mM phosphate containing 4 mg/mL PLURONIC F68. The disk was washed with 2 mL of 50 mM phosphate containing 4 mg/mL PLURONIC F68 followed by two 2 mL aliquots of 400 mM phosphate containing 4 mg/mL PLURONIC F68. As measured by the 260 nm absorbance of the filtrates, the DNA adhered completely and did not elute at 50 mM phosphate but at least 90% did elute when the phosphate concentration was raised to 400 mM.

In another experiment a fresh 25 mm disk was charged with 2 mL of about 35 µg/mL DNA in 50 mM phosphate, washed with a single 2 mL wash of 50 mM phosphate and three 2 mL washes of 400 mM phosphate and finally two 2 mL washes of 400 mM phosphate containing 4 mg/mL of PLURONIC F68. Again the DNA bound to the membrane but did not elute (even at the higher phosphate concentration) until the membrane was treated with the PLURONIC containing high phosphate buffer. The results, reported as the absorbance at 260 nm, were as follows:

| Sample | PLURONIC F68 in DNA and all buffers | PLURONIC F68 only in final 0.4M phosphate wash |
| --- | --- | --- |
| DNA challenge | 0.45 | 0.41 |
| 50 mM phosphate wash | 0.03 | 0.03 |
| 1st 400 mM phosphate | 0.40 | 0.03 |
| 2nd 400 mM phosphate | 0.05 | 0.03 |
| 3rd 400 mM phosphate | — | 0.03 |
| 1st phosphate/PLURONIC | — | 0.31 |
| 2nd phosphate/PLURONIC | — | 0.05 |

These results indicate that when PLURONIC F68 is present the membrane behaves like HAP; however when it is absent the membrane fails to elute DNA.

Example 3

Adherance of DNA Utilizing Polypropylene-Loaded and C18-Loaded EMPORE Membranes A polypropylene-loaded (prepared from Himont powdered polypropylene, Montell North America, Wilmington, Del.) and a C18-loaded EMPORE membrane were used in experiments in a manner similar to the HAP-loaded membrane. Both membranes were preconditioned by washing with 5 mL of methanol followed by 5 mL of water, followed by 5 mL of 400 mM phosphate buffer. The challenge solution was approximately 60 $\mu$g/mL of calf thymus DNA in 400 mM phosphate buffer. Two 1 mL aliquots of this solution were applied to the membrane followed by four 1 mL washes with 400 mM phosphate and the four 1 mL washes with 50 mg/mL PLURONIC F68 in water. The filtrates were monitored at 260 nm for DNA levels. The results, reported as the UV absorbance at 260 nm, were as follows:

| Sample | Polypropylene membrane Absorbance at 260 nm | C18 membrane Absorbance at 260 nm |
|---|---|---|
| Challenge DNA solution | 0.746 | 0.746 |
| 1st mL DNA | 0.04 | 0.06 |
| 2nd mL DNA | 0.04 | 0.04 |
| 1st mL Phosphate wash | 0.03 | 0.04 |
| 2nd mL Phosphate wash | 0.04 | 0.04 |
| 3rd mL Phosphate wash | 0.04 | 0.04 |
| 4th mL Phosphate wash | 0.04 | 0.03 |
| 1st mL Pluronic F68 wash | 0.78 | 0.61 |
| 2nd mL Pluronic F68 wash | 0.34 | 0.35 |
| 3rd mL Pluronic F68 wash | 0.14 | 0.11 |
| 4th mL Pluronic F68 wash | 0.08 | 0.07 |

These results show that the DNA adhered to both the polypropylene and the C18 Empore membrane and that it could be desorbed with the PLURONIC F68. Recoveries were nearly 90% for the polypropylene membrane and about 75% for the C18. Other nonionic surfactants such as PLURONIC L31, TWEEN 20, TERGITOL MN6, and NONIDET P40 all behaved similar to the PLURONIC F68 in facilitating elution of the nucleic acid under these conditions.

Example 4

Difference Between the Adherance of Single-stranded and Double-stranded DNA

When double stranded DNA (dsDNA) is boiled it will denature into single stranded DNA (ssDNA). When brought back to about room temperature the DNA will only very slowly return to dsDNA. In the following experiment an 50 $\mu$g/mL solution of DNA in 10 mM phosphate buffer was split in two. One half was boiled for ten minutes, cooled to room temperature, and tested immediately while the other half was tested directly without boiling. Disks (25 mm in diameter) of a polypropylene-loaded EMPORE membrane (prepared from MICROPRO 600 polypropylene powder, Micro Powders, Inc., Tarrytown, N.Y.) were challenged with these two solutions and the absorbance at 260 nm of the filtrate measured to determine how much DNA adhered.

Half of the DNA solution was boiled for ten minutes and quickly cooled to room temperature just prior to use. The absorbance at 260 nm was 1.014 before boiling and 1.26 just after boiling. The boiled (denatured) and native solutions where used to challenge the EMPORE membrane and the optical density of the filtrate monitored. The membranes were conditioned by washing with methanol, followed by water, followed by 10 mM phosphate buffer as described in Example 3. The results, reported as the absorbance at 260 nm, were as follows:

| mL DNA challenge | Native DNA (ds DNA) | BoiledDNA (ss DNA) |
|---|---|---|
| 1 | 0.00 | 0.0425 |
| 2 | — | 0.2665 |
| 3 | — | 0.5173 |
| 4 | — | 0.6932 |
| 5 | 0.013 | 0.8109 |
| 6 | — | 0.9147 |
| 7 | — | 0.9577 |
| 8 | — | — |
| 9 | — | — |
| 10 | 0.050 | — |

As is evident from these experiments the native DNA had a much higher affinity for the membrane than the denatured (single-stranded) DNA. This difference in affinity could be used to separate single from double-stranded DNA.

Example 5

Use of the EMPORE Membrane and Nonionic Surfactant to Purify Plasmid DNA

The following experiment shows that plasmid DNA can adhere to a polypropylene-loaded EMPORE membrane (prepared from MICROPRO 600 polypropylene powder, Micro Powders, Inc., Tarrytown, N.Y.) and eluted with a nonionic surfactant. In one case the eluted plasmid is separated from contaminants.

A 25 mm disk of the membrane was put in a syringe filter holder and primed by washing with 5 mL of ethanol followed by 5 mL of water followed by the challenge buffer (10 or 400 mm phosphate at pH 6.8). Three mL of the plasmid DNA solution was passed through the membrane with the aid of a syringe and the filtrate collected. Three mL of 0.5% PLUROINC F68 in 10 mM phosphate (pH 6.8) was then used to elute the plasmid DNA. The optical densities at 260 nm of the starting challenge solution the filtrate and the eluate were then measured. Fifty $\mu$L of each solution was mixed with 5 $\mu$L of standard gel loading dye. Five $\mu$L of this solution was then analyzed by agarose electrophoresis. The results, reported as absorbance at 260 nm, were as follows:

| Sample | 400 mM Phosphate | 10 mM Phosphate |
|---|---|---|
| Challenge sol. | 0.585 | 0.601 |
| Filtrate | 0.025 | 0.091 |
| Eluate | 0.282 | 0.251 |

Electrophoresis Results: at 400 mM phosphate challenge all of the challenge adhered and nothing was seen in the filtrate. When the membrane was eluted with the PLURONIC surfactant about half of the plasmid was recovered but the purity of the eluted plasmid DNA was about the same as in the challenge. When the challenge was made in 10 mM buffer, the eluate contained the lower molecular weight bands that were contaminating the plasmid. The eluate contained the now purified plasmid.

Example 6

Adherance of DNA to a Polypropylene TIPS Membrane and Elution with a Nonionic Surfactant

Three 2.54 cm diameter circles were cut from a polypropylene TIPS membrane (100 microns thick, density=0.153 grams/cubic cm), placed in a syringe filter holder (MSI Inc., Westboro, Mass. 01581) and washed with 5 mL of methanol followed by 5 mL of water. Three mL of a 200 μg/mL solution of calf thymus DNA in 100 mM sodium phosphate buffer at pH 7.2 was passed through the filter stack in the filter holder followed by 3 mL of 10 mg/mL of PLURONIC F68 nonionic surfactant in the phosphate buffer. UV absorbance at 260 nm was used to determine the amount of DNA in these solutions, and the results were as follows:

| Solution | Absorbance at 260 nm |
| --- | --- |
| DNA challenge | 1.95 |
| DNA challenge after passing through filters | 0.00 |
| PLURONIC F68 in buffer (blank) | 0.03 |
| PLURONIC F68 wash | 1.80 |

These results show that the DNA binds to the polypropylene TIPS membrane and is eluted with a solution of the PLURONIC F68.

Example 7

Adherance of DNA to a Polyethylene TIPS Membrane and Elution with a Nonionic Surfactant

A single 2.54 cm diameter circle was cut from a polyethylene TIPS membrane (120 microns thick, density=0.186 grams/cubic cm) and placed in the syringe filter holder. The membrane was washed with 5 mL of methanol followed by 5 mL of water and challenged with 3 mL of 17 micrograms/mL of calf thymus DNA in a 50 mM AMPSO buffer (3-[(1,1dimethyl-2-hydroxyethyl)amino]-2-hydroxypropanesulfonic acid (#A7585, Sigma Chemical Co, St. Louis, Mo. 63178) buffer at pH 9.0 and containing 100 mM of sodium chloride. The filter was then eluted with 3 mL of 5 mg/mL of PLURONIC F68 in the same buffer. UV absorbance at 260 nm was used to determine the concentration of DNA in these solutions.

| Solution | Absorbance at 260 nm |
| --- | --- |
| Challenge DNA solution | 0.339 |
| Challenge after passing through the filter | 0.015 |
| PLURONIC F68 in buffer (blank) | 0.01 |
| PLURONIC after passing through the filter | 0.195 |

These results show that the polyethylene filter would bind DNA and that it could be eluted with PLURONIC F68.

Example 8

Use of a Nonionic to Prevent DNA from Adhering to the Polypropylene Membrane

In this experiment the polypropylene TIPS membrane was washed with a nonionic detergent followed by a second wash using the same buffer in which the nonionic was dissolved. The resulting treatment effectively blocked nucleic acid from adhering to the surface. A 2.54 cm diameter circle of the polypropylene TIPS membrane was placed in the filter holder and washed with 5 mL of methanol followed by 5 mL of water, 5 mL of 10 mg/mL of PLURONIC F68 in 20 mM AMPSO, 100 mM sodium chloride buffer at pH 9.0, and finally 5 mL of the AMPSO, sodium chloride buffer. It was then challenged with two 3 mL samples of 15 μg/mL of calf thymus DNA in the AMPSO, sodium chloride buffer. UV absorbance at 260 nm was used to determine DNA concentrations.

| Solution | Absorbance at 260 nm |
| --- | --- |
| Challenge DNA solution | 0.317 |
| First sample after passing through the filter | 0.247 |
| Second sample after passing through the filter | 0.306 |

The first sample passing through the filter had a lower absorbance than the challenge due to some dilution from residual wash solution in the filter holder. The second sample had nearly as much DNA in it as the challenge. This experiment was repeated using the same conditions except that the buffer was a 20 mM MES buffer (2-[N-morpholino] ethansulfonic acid) (#M5287, Sigma Chemical Co, St. Louis, Mo. 63178) at pH 6.0. The results were essentially the same. These results show that a nonionic detergent such as PLURONIC F68 can passivate a polymer surface so that nucleic acid will not bind to it. This passivation endures even after the polymer surface is washed with buffer, which was the solvent for the nonionic surfactant.

Example 9

Adherance of RNA to a TIPS Membrane

Three one inch diameter polypropylene TIPS membrane were stacked in a filter holder and washed with 5 mL of methanol followed by 5 mL of distilled water followed by 5 mL of 50 mM MES buffer at pH 6.0. Two mL of 50 μM/mL ribonucleic acid (Sigma) in the same MES buffer was passed through the filter stack. The stack was then washed with 2 mL of the MES buffer and then eluted with 2 mL of 0.5% PLURONIC F68 in the MES buffer. The amount of RNA in each of these stages was monitored by UV absorbance at 260 nm.

| Solution | Absorbance at 260 nm |
| --- | --- |
| Initial RNA solution | 1.13 |
| After TIPS membrane | 0.02 |
| Buffer wash | 0.03 |
| Pluronic elution | 0.61 |

The RNA completely adhered to the TIPS membrane and was resistant to desorption by the buffer alone but over half eluted with the PLURONIC F68 nonionic surfactant

Example 10

Adherance and Elution of a Small DNA Oligomer

In the following experiment the hydrophobic polypropylene TIPS membrane was challenged with a very small oligomer of DNA and then washed and eluted with the nonionic surfactant. The DNA oligomer was a 22-mer of single-stranded DNA with a melting temperature of 65.8° C., which was purchased from Genosys Biotechnologies, Inc. Woodlands, Tex. 77380. It is referred to as Oligo22. Three 25 mm diameter polypropylene TIPS membranes were stacked in a syringe filter holder and washed with 5 mL of methanol followed by 5 mL of water and 5 mL of 50 mM MES buffer at pH 6.0. The filter stack was then challenged with 2 mL of a 38 microgram/mL solution of Oligo22 in the MES buffer. The filtrate was collected and the stack washed with 2 mL of the MES buffer followed by 2 mL of PLURONIC F68 nonionic surfactant in the MES buffer. Levels of the Oligo22 in the challenge filtrate and washes were monitored by UV absorbance at 260 nm.

| Solution | Absorbance at 260 nm |
|---|---|
| Challenge | 1.19 |
| Challenge filtrate | 0.01 |
| MES buffer wash | 0.01 |
| Pluronic wash | 1.17 |

The results show that the small oligomer effectively adhered to the polypropylene TIPS membrane and was eluted with the nonionic surfactant.

Example 11

Binding of RNA to a Polypropylene TIPS Membrane and Elution with TWEEN 60 Nonionic Surfactant Three one inch diameter polypropylene TIPS membrane were stacked in a filter holder and washed with 5 mL of methanol followed by 5 mL of distilled water followed by 5 mL of 50 mM MES buffer at pH 6.0. Then, 2 mL of 50 $\mu$M/mL ribonucleic acid (Sigma #R7125) in the same MES buffer was passed through the filter stack. The stack was then washed with 2 mL of the MES buffer and then eluted with 2 mL of polyoxyethylenesorbitan monostearate (Tween 60, #P1629, Sigma Chemical Co., St. Louis Mo. 63178) in the MES buffer. The amount of RNA in each of these stages was monitored by UV absorbance at 260 nm. The results were as follows:

| Solution | Absorbance at 260 nm |
|---|---|
| Initial RNA solution | 1.11 |
| After TIPS membrane | 0.03 |
| Buffer wash | 0.01 |
| Pluronic elution | 0.76 |

The RNA completely adsorbed on to the TIPS membrane and was resistant to desorption by the buffer alone but over half eluted with the polyoxyethylenesorbitan monostearate nonionic surfactant.

Comparative Example 1

Adhesion and Elution of RNA from a Hydrophilic Membrane

The following experiment shows that hydrophilic membranes will not bind nucleic acids and so cannot be used for this nucleic acid extraction technique.

Three 25 mm MSI cellulose acetate membranes (MSI, Westboro, Mass. 01581) were placed in a syringe filter holder and washed with 5 mL of water followed by 5 mL of 50 mM AMPSO buffer at pH 9.0. The filter stack was then challenged with 2 mL of 50 $\mu$g/mL RNA (Sigma Chemical Co, St. Louis, Mo. 63178) and then washed with 2 mL of the AMPSO buffer followed by 2 mL of 0.5% PLURONIC F68 in the AMPSO buffer. The amount of RNA in each of these eluates was monitored by UV absorbance at 260 nm. This experiment was repeated using 50 mM MES buffer at pH 6.0 and at both pH's with a cellulose filter (Osmonics Inc.).

Of the 100 $\mu$g of RNA challenge, 73 $\mu$g was in the filtrate and the rest (27 $\mu$g) was in the first buffer wash. No RNA was found in the PLURONIC F68 wash. Similar results were obtained at pH 9.0 and with the cellulose filter. These results show that nucleic acids will not adsorb onto these hydrophilic membranes.

The complete disclosures of the patents, patent documents, and publications cited herein are incorporated by reference in their entirety as if each were individually incorporated. Various modifications and alterations to this invention will become apparent to those skilled in the art without departing from the scope of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method for isolating nucleic acid from a sample, the method comprising:
   introducing a sample comprising target nucleic acid to a hydrophobic organic polymeric solid phase to adhere at least a portion of the target nucleic acid to the solid phase; and
   applying a nonionic surfactant to the solid phase to remove at least a portion of the adhered target nucleic acid.

2. The method of claim 1 wherein the sample comprises a biological sample.

3. The method of claim 2 wherein the biological sample comprises cells.

4. The method of claim 3 wherein prior to introducing the biological sample, the method comprises lysing the cells to release the contents of the cells as a lysate comprising nucleic acid.

5. The method of claim 4 wherein the biological sample comprises whole blood, blood serum, urine, saliva, tissue, or a cell culture.

6. The method of claim 3 wherein the cells are mammalian, bacterial cells, yeast cells, or plant cells.

7. The method of claim 1 wherein the target nucleic acid comprises DNA.

8. The method of claim 7 wherein the DNA comprises double-stranded DNA.

9. The method of claim 7 wherein the DNA comprises single-stranded DNA.

10. The method of claim 1 wherein the target nucleic acid comprises RNA.

11. The method of claim 1 wherein the target nucleic acid comprises PNA.

12. The method of claim 1 wherein the target nucleic acid comprises plasmid DNA.

13. The method of claim 1 further comprising introducing a binding buffer comprising an added salt to the hydrophobic organic polymeric solid phase to assist in adhering the nucleic acid to the solid phase.

14. The method of claim 13 wherein the binding buffer is introduced prior to introducing the sample comprising nucleic acid.

15. The method of claim 1 further comprising washing the solid phase having target nucleic acid adhered thereto to remove non-nucleic acid components of the sample.

16. The method of claim 15 wherein washing comprises washing with a washing buffer comprising an added salt.

17. The method of claim 1 wherein the hydrophobic organic polymeric solid phase comprises a polyolefin.

18. The method of claim 17 wherein the polyolefin comprises polypropylene.

19. The method of claim 17 wherein the polyolefin comprises polyethylene.

20. The method of claim 1 wherein the hydrophobic organic polymeric solid phase comprises a fluorinated polymer.

21. The method of claim 20 wherein the fluorinated polymer comprises polytetrafluoroethylene.

22. The method of claim 1 wherein the nonionic surfactant is selected from the group of polyoxyethylene surfactants.

23. The method of claim 22 wherein the nonionic surfactant is selected from the group of polyoxyethylene-co-oxypropylene surfactants.

24. The method of claim 1 wherein the nucleic acid is collected in a substantially purified form from the sample.

25. The method of claim 1 wherein the hydrophobic organic polymeric solid phase is in the form of a porous matrix.

26. The method of claim 24 wherein the surface area of the solid phase is at least about 1 meter square per gram.

27. A method for isolating double-stranded DNA from a sample, the method comprising:

introducing a sample comprising double-stranded DNA to a hydrophobic organic polymeric solid phase to adhere at least a portion of the double-stranded DNA to the solid phase;

washing the solid phase having double-stranded DNA adhered thereto to remove non-double-stranded DNA components of the sample; and applying a nonionic surfactant to the solid phase to remove at least a portion of the adhered double-stranded DNA.

28. The method of claim 27 wherein washing comprises washing with a washing buffer comprising an added salt.

29. The method of claim 27 further comprising introducing a binding buffer comprising an added salt to the hydrophobic organic polymeric solid phase to assist in adhering the nucleic acid to the solid phase.

30. The method of claim 29 wherein the binding buffer is introduced prior to introducing the sample comprising nucleic acid.

31. The method of claim 27 wherein the hydrophobic organic polymeric solid phase comprises a polyolefin.

32. The method of claim 27 wherein the hydrophobic organic polymeric solid phase comprises a fluorinated polymer.

* * * * *